US012629082B2

(12) United States Patent
Mahajan et al.

(10) Patent No.: US 12,629,082 B2
(45) Date of Patent: May 19, 2026

(54) SYSTEMS AND METHODS FOR DETECTING ATRIAL TACHYARRHYTHMIA

(71) Applicant: Cardiac Pacemakers, Inc., St. Paul, MN (US)

(72) Inventors: Deepa Mahajan, North Oaks, MN (US); David L. Perschbacher, Blaine, MN (US); Sunipa Saha, Shoreview, MN (US); Abhijit Rajan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 506 days.

(21) Appl. No.: 17/489,413

(22) Filed: Sep. 29, 2021

(65) Prior Publication Data

US 2022/0095983 A1     Mar. 31, 2022

Related U.S. Application Data

(60) Provisional application No. 63/085,613, filed on Sep. 30, 2020.

(51) Int. Cl.
| | |
|---|---|
| *A61B 5/363* | (2021.01) |
| *A61B 5/00* | (2006.01) |
| *A61B 5/024* | (2006.01) |
| *A61B 5/29* | (2021.01) |

(52) U.S. Cl.
CPC .......... *A61B 5/363* (2021.01); *A61B 5/02405* (2013.01); *A61B 5/29* (2021.01); *A61B 5/7246* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 7,412,282 B2 | 8/2008 | Houben | |
| 8,560,058 B2 * | 10/2013 | Babaeizadeh | A61B 5/361 |
| | | | 600/518 |
| 10,702,180 B2 | 7/2020 | Perschbacher et al. | |
| 10,744,334 B2 | 8/2020 | Perschbacher et al. | |
| 11,051,746 B2 | 7/2021 | Krueger et al. | |
| 2002/0143266 A1 * | 10/2002 | Bock | A61B 5/7264 |
| | | | 600/518 |
| 2004/0215257 A1 * | 10/2004 | Van Oort | A61N 1/368 |
| | | | 607/9 |
| 2011/0125206 A1 * | 5/2011 | Bornzin | A61B 5/287 |
| | | | 600/518 |

(Continued)

*Primary Examiner* — William J Levicky
*Assistant Examiner* — Willow Grace Welch
(74) *Attorney, Agent, or Firm* — Nelson Mullins Riley & Scarborough LLP

(57) ABSTRACT

Systems and methods for detecting cardiac arrhythmia are discussed. A medical-device system includes an arrhythmia detector circuit and an event prioritizer circuit. The arrhythmia detector circuit can detect an atrial activation event from a cardiac electrical signal sensed from the patient, and determine an atrial fibrillation (AF) confidence indicator based on a signal characteristic of the atrial activation event. The event prioritizer circuit can generate an event priority for the AF event based on the AF confidence indicator. Multiple AF events may be prioritized in a specific order and presented to a user or a process.

19 Claims, 7 Drawing Sheets

(56)          References Cited

U.S. PATENT DOCUMENTS

| 2011/0184297 | A1* | 7/2011 | Vitali | A61B 5/316 |
| | | | | 600/509 |
| 2011/0319779 | A1* | 12/2011 | Sweeney | A61N 1/36514 |
| | | | | 600/515 |
| 2014/0128758 | A1* | 5/2014 | Galloway | A61B 5/02438 |
| | | | | 600/521 |
| 2015/0343223 | A1* | 12/2015 | Thakur | A61B 5/361 |
| | | | | 607/18 |
| 2016/0045125 | A1* | 2/2016 | Krueger | A61B 5/02405 |
| | | | | 600/518 |
| 2017/0290550 | A1* | 10/2017 | Perschbacher | A61B 5/076 |
| 2019/0231207 | A1* | 8/2019 | Perschbacher | G16H 15/00 |
| 2020/0077914 | A1* | 3/2020 | Siejko | A61B 5/352 |

* cited by examiner

310

330

500

510

RECEIVE A CARDIAC ELECTRICAL SIGNAL

520

DETECT AN AF EVENT AND AN ATRIAL ACTIVATION EVENT

530

DETERMINE A CONFIDENCE INDICATOR OF THE AF EVENT
BASED ON A SIGNAL CHARACTERISTIC OF THE ATRIAL
ACTIVATION EVENT

540

GENERATE AN EVENT PRIORITY INDICATOR FOR THE AF
EPISODE

550

PRESENT THE AF EPISODE TO A USER OR A PROCESS
ACCORDING TO THE EVEN PRIORITY

SYSTEMS AND METHODS FOR DETECTING ATRIAL TACHYARRHYTHMIA

CLAIM OF PRIORITY

This application claims the benefit of priority under 35 U.S.C. § 119(e) of U.S. Provisional Patent Application Ser. No. 63/085,613, filed on Sep. 30, 2020, which is herein incorporated by reference in its entirety.

TECHNICAL FIELD

This document relates generally to medical devices, and more particularly, to systems, devices, and methods for detecting atrial tachyarrhythmia.

BACKGROUND

Implantable medical devices (IMDs) have been used for monitoring patient health condition or disease states and delivering therapies. For example, implantable cardioverter-defibrillators (ICDs) may be used to monitor certain abnormal heart rhythms and to deliver electrical energy to the heart to correct the abnormal rhythms. Some IMDs may be used to monitor chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmia, such as atrial arrhythmia. One type of atrial arrhythmia is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Timely detection of atrial arrhythmia may be clinically important for assessing cardiac function. Atrial tachyarrhythmia may be characterized by fast atrial rate and irregular ventricular rates. However, irregular ventricular rates can be a caused by confounding factors such as respiration-mediated sinus arrhythmia, and affect atrial arrhythmia detection specificity. Inappropriate atrial arrhythmia detection may have adverse impact on patient outcome.

Overview

This document discusses, among other things, systems, devices, and methods for detecting cardiac arrhythmia, such as atrial fibrillation (AF). A medical-device system includes an arrhythmia detector circuit to detect an atrial activation event from a cardiac electrical signal sensed from the patient, and to determine an AF confidence indicator based on a signal characteristic of the atrial activation event. The AF confidence indicator indicates a likelihood of an AF event being present. The system includes an event prioritizer circuit configured to generate an event priority for the AF event based on the AF confidence indicator. Multiple AF events may be prioritized in a specific order. The ordered AF events may be displayed to a user, or provided to a process for further analysis.

Example 1 is a medical-device system for detecting cardiac arrhythmia in a patient, the system comprising an arrhythmia detector circuit and an event prioritizer circuit. The arrhythmia detector is configured to: receive a cardiac electrical signal sensed from the patient; detect an atrial fibrillation (AF) event using the cardiac electrical signal; detect an atrial activation event from a cardiac electrical signal; and based at least on a signal characteristic of the detected atrial activation event, determine an AF confidence indicator indicating a confidence level of the detected AF event. The event prioritizer circuit is configured to generate an event priority for the AF event based on the AF confidence indicator.

In Example 2, the subject matter of Example 1 optionally includes the arrhythmia detector circuit that can be configured to detect the atrial activation event from an ensemble average of segments of the cardiac electrical signal corresponding to a plurality of cardiac cycles.

In Example 3, the subject matter of Example 2 optionally includes the arrhythmia detector circuit that can be configured to generate the signal characteristic including a peak intensity or a signal power of the detected atrial activation event.

In Example 4, the subject matter of any one or more of Examples 1-3 optionally includes the arrhythmia detector circuit that can be configured to: detect a plurality of atrial activation events respectively from segments of the cardiac electrical signal corresponding to a plurality of cardiac cycles; generate signal characteristics respectively from the plurality of atrial activation events; and determine the AF confidence indicator based on a variability of the signal characteristics of the plurality of atrial activation events.

In Example 5, the subject matter of Example 4 optionally includes the arrhythmia detector circuit that can be configured to: generate the signal characteristics including similarity metrics between (1) an ensemble-averaged morphology of the plurality of atrial activation events and (2) respective signal morphologies of the plurality of atrial activation events; and determine the AF confidence indicator based on a variability of the similarity metrics.

In Example 6, the subject matter of any one or more of Examples 4-5 optionally includes the arrhythmia detector circuit that can be configured to: generate the signal characteristics including similarity metrics between (1) an atrial morphology template acquired during a specific type of cardiac rhythm and (2) respective signal morphologies of the atrial activation events; and determine the AF confidence indicator based on a variability of the similarity metrics.

In Example 7, the subject matter of Example 6 optionally includes the specific type of cardiac rhythm which can be a normal sinus rhythm.

In Example 8, the subject matter of any one or more of Examples 1-7 optionally includes the arrhythmia detector circuit that can be configured to detect a ventricular activation event in a cardiac cycle, and to detect the atrial activation event based on a peak intensity of the cardiac electrical signal within a detection window preceding the detected ventricular activation event within the cardiac cycle.

In Example 9, the subject matter of any one or more of Examples 1-8 optionally includes the arrhythmia detector circuit that can be configured to detect a ventricular activation event in a cardiac cycle, and to detect the atrial activation event based on a dominant frequency of the cardiac electrical signal within a detection window preceding the detected ventricular activation event within the cardiac cycle.

In Example 10, the subject matter of any one or more of Examples 1-9 optionally includes the arrhythmia detector circuit that can be configured to: detect a noise level from the cardiac electrical signal within a noise window; filter the cardiac electrical signal using the detected noise level; and detect the atrial activation event using the filtered cardiac electrical signal.

In Example 11, the subject matter of any one or more of Examples 1-10 optionally includes the arrhythmia detector circuit that can be configured to determine respective AF confidence indicators for two or more AF events detected from the patient; and the event prioritizer circuit that can be configured to prioritize the two or more AF events in a descending order of the AF confidence indicators.

In Example 12, the subject matter of Example 11 optionally includes a display configured to present to a user respective portions of the two or more AF events in a descending order of the AF confidence indicators.

Example 13 is a system for detecting cardiac arrhythmia in a patient, comprising an ambulatory medical device and an external system. The ambulatory medical device is configured to sense a cardiac electrical signal from the patient, and to detect an atrial fibrillation (AF) event using the cardiac electrical signal. The external system, communicatively coupled to the ambulatory medical device, can include: an arrhythmia detector circuit configured to detect an atrial activation event from the sensed cardiac electrical signal, and based at least on a signal characteristic of the detected atrial activation event, determine an AF confidence indicator indicating a confidence level of the detected AF event; an event prioritizer circuit configured to generate an event priority for the AF event based on the AF confidence indicator; and a user interface configured to present to a user the AF event and the AF confidence indicator for the sensed cardiac electrical signal.

In Example 14, the subject matter of Example 13 optionally includes the ambulatory medical device which can be an implantable cardiac monitor.

In Example 15, the subject matter of any one or more of Examples 13-14 optionally includes the arrhythmia detector circuit that can be configured to determine respective AF confidence indicators for two or more AF events from the patient; the event prioritizer circuit is configured to prioritize the two or more AF events based on the respective AF confidence indicators; and the user interface that can be configured display portions of the AF events in a descending order of the AF confidence indicators.

Example 16 is a method for detecting cardiac arrhythmia in a patient. The method comprises steps of: receiving a cardiac electrical signal sensed from the patient; detecting, using an arrhythmia detector circuit, an atrial fibrillation (AF) event using the cardiac electrical signal; detecting, using the arrhythmia detector circuit, an atrial activation event from the cardiac electrical signal; based at least on a signal characteristic of the detected atrial activation event, determining an AF confidence indicator indicating a confidence level of the detected AF event; and generating, using an event prioritizer circuit, an event priority for the AF event based on the AF confidence indicator.

In Example 17, the subject matter of Example 16 optionally includes generating an ensemble average of segments of the cardiac electrical signal corresponding to a plurality of cardiac cycles, and wherein detecting an atrial activation event is from the ensemble average of the segments of the cardiac electrical signal.

In Example 18, the subject matter of any one or more of Examples 16-17 optionally includes the signal characteristic that can include a peak intensity or a signal power of the atrial activation event, and the atrial fibrillation (AF) confidence indicator is determined to be inversely proportional to the peak intensity or the signal power of the atrial activation event.

In Example 19, the subject matter of any one or more of Examples 16-18 optionally includes: detecting the atrial activation event includes detecting a plurality of atrial activation events respectively from segments of the cardiac electrical signal corresponding to a plurality of cardiac cycles; and determining the AF confidence indicator includes generating signal characteristics respectively from the plurality of atrial activation events, and determining the AF confidence indicator based on a variability of the signal characteristics of the plurality of atrial activation events.

In Example 20, the subject matter of Example 19 optionally includes: generating the signal characteristics from the plurality of atrial activation events that can include calculating similarity metrics between (1) an ensemble-averaged morphology of the plurality of atrial activation events and (2) respective signal morphologies of the plurality of atrial activation events; and determining the AF confidence indicator is based on a variability of the similarity metrics.

In Example 21, the subject matter of any one or more of Examples 19-20 optionally includes: generating the signal characteristics from the plurality of atrial activation events that can include calculating similarity metrics between (1) an atrial morphology template acquired during a specific type of cardiac rhythm and (2) respective signal morphologies of the atrial activation events; and determining the AF confidence indicator is based on a variability of the similarity metrics.

In Example 22, the subject matter of any one or more of Examples 16-21 optionally includes: determining respective AF confidence indicators for two or more AF events detected from the patient; and prioritizing the two or more AF events in a descending order of the AF confidence indicators.

In Example 23, the subject matter of Example 22 optionally includes displaying, on a display, two or more AF events in a descending order of the AF confidence indicators.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
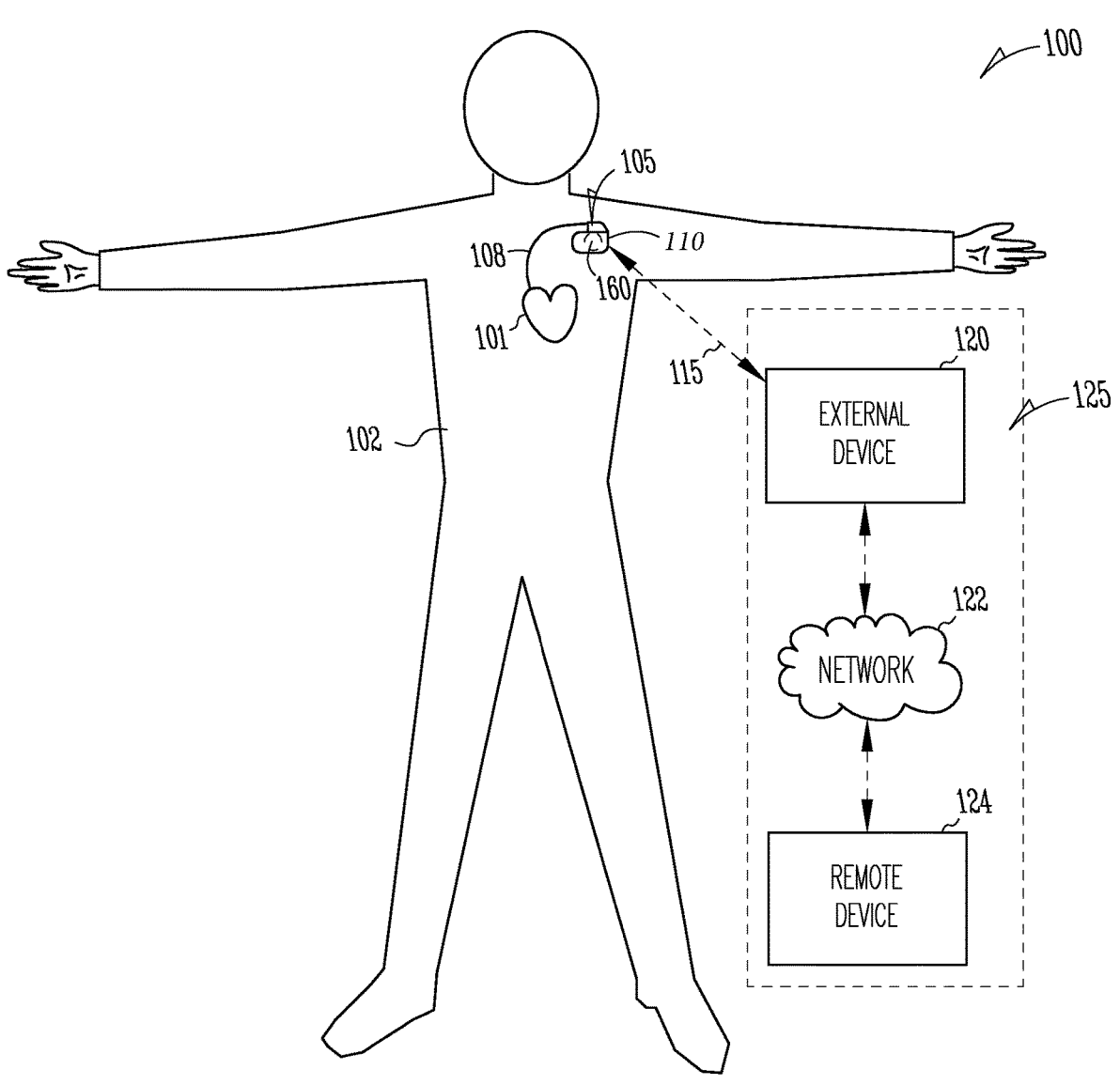
FIG. 1 illustrates generally an example of a patient management system and portions of an environment in which the system may operate.

Some IMDs are capable of detecting physiologic events, such as cardiac arrhythmias or progression of chronic heart diseases, and obtaining sampled values of cardiac electrical activity signals such as electrograms. Some IMDs may be communicated with multiple physiologic sensors that may measure various physiologic signals. Capturing accurate electrogram or other physiologic sensor information obtained over a longer period of time, such as chronically between regularly-scheduled outpatient office visits, may help the physician re-program the device, if needed, diagnose cardiac disease, or assess the patient's health status.

Atrial tachyarrhythmia is characterized by fast atrial rate. In some patients, direct sensing of atrial activation rate with an electrode positioned in the atrium is not available or not feasible, such as in patients not indicated for atrial lead implantation. A medical device, such as a single-chamber IMD with no dedicated atrial sensing/pacing lead, may detect the atrial arrhythmia based on sensed ventricular activity (e.g., ventricular heart rates), instead of direct sensing of atrial activity from the atrium. At least due to the refractoriness of the AV node, ventricular rates may be irregular during AF or AFL. However, irregular ventricular rates may also be caused by confounding factors, such as noise, motion artifacts, variation in timing of cardiac events being detected, cardiac rhythms with a non-atrial origin, higher variation in sinus rate, respiratory sinus arrhythmia, wandering atrial pacemaker rhythm, or vagus nerve stimulation such as via baroreflex activation. Therefore, an atrial arrhythmia detected based on irregular ventricular rates may be a false positive detection. False positive detection may decrease the detection specificity, and lead to inappropriate or unnecessary interventions. On the other hand, in some instances, a true atrial arrhythmia event may be misrecognized as an aberrancy such as due to conduction abnormality at a bundle branch (e.g., rate-dependent bundle branch block), resulting in false negative detections of atrial arrhythmia.

Both false positive and false negative detections have an adverse impact on arrhythmia detection efficacy, and may unwarrantedly increase the healthcare cost for patient management. For example, false alarms of the inappropriately detected atrial arrhythmia, or presenting to clinicians a large volume of inappropriately detected arrhythmic events for review or adjudication, may diminish the clinical utility of arrhythmia detection feature in a medical device. False negative detections may decrease atrial arrhythmia detection sensitivity, causing a delay in antiarrhythmic therapies or other medical interventions.

The present inventors have recognized an unmet need for arrhythmia detection systems and methods with improved arrhythmia detection performance (e.g., sensitivity and specification). Improved performance may be achieved using more computationally intensive algorithms or more individualized device programming, which generally require more system resources (e.g., more power and memory usage in an implantable device) and/or human effort (e.g., clinician reviewing and adjudicating device-detected arrhythmia events). Determining a detection confidence for a device-detected arrhythmic event and distinguishing arrhythmic events with a high confidence from those with a low confidence may allow the system and human resources to be better aligned with patient needs. For example, high-confidence events may be presented to the user ahead of the low-confidence events, or the low-confidence events may be further processed to confirm the presence of arrhythmia using a computationally more intensive algorithm. This may improve the overall arrhythmia detection performance without overusing the available resources.

Disclosed herein are systems, devices, and methods for detecting cardiac arrhythmia, such as atrial arrhythmia. A medical-device system includes an arrhythmia detector circuit and an event prioritizer circuit. The arrhythmia detector circuit may detect an atrial activation event from a cardiac electrical signal sensed from the patient, and determine an atrial fibrillation (AF) confidence indicator based on a signal characteristic of the atrial activation event. The AF confidence indicator indicates a likelihood of an AF event being present. Based on the AF confidence, the event prioritizer circuit may generate an event priority for the AF event. The event prioritizer circuit may prioritize a plurality of device-detected AF events in a specific order. The AF events may be displayed to a user, or presented to a process for further analysis, in accordance with the prioritized order.

The systems, devices, and methods discussed in this document may improve the medical technology of device-based arrhythmia detection, particularly detection of AF events. According to some examples, a device-detected AF event may be evaluated for a detection confidence using a signal characteristic of an atrial activation event, such as a P wave in a surface ECG or a subcutaneous ECG, such as sensed by an implantable cardiac monitor (ICM). The atrial activation event may be detected from an ensemble average of segments of a cardiac electrical signal over a plurality of cardiac cycles. The signal characteristic may include signal intensity, signal power, or signal morphology of the atrial activation event. An AF confidence indicator may be generated based on the signal characteristic of the atrial activation event. The use of the signal characteristic of the atrial activation event as discussed herein may help improve atrial arrhythmia detection sensitivity and specificity, thereby reducing healthcare cost associated with false AF detections. Additionally, the improvements in AF detection may be achieved with little to no additional cost or added system complexity. In some examples, existing system performance may be maintained (e.g., high arrhythmia detection sensitivity and specificity, etc.) using lower cost or less obtrusive systems, apparatus, and methods. With improved AF detection, fewer alarms are provided, battery life may be extended, fewer unnecessary drugs and procedures may be scheduled, prescribed, or provided, and an overall system cost and power savings may be realized in contrast to existing medical devices and systems.

According to various examples discussed herein, the device-detected AF events may be prioritized in an order of AF confidence indicators determined based on the atrial event characteristics. The ordered AF events may be presented to a clinician for event data review, adjudication, or further data processing. This may improve over the conventional medical data management and alert system, where a high volume of device-detected medical events (e.g., arrhythmia events) and associated alerts are presented to a user (e.g., a clinician). Reviewing and processing device-detected medical events with mixed or unidentified certainties may put a high demand for time, effort, and resources, and can be costly for a healthcare facility. The presently discussed events prioritization based on arrhythmia detection confidence may substantially reduce users' burden of handling the device-detected medical events, such that they may direct their attention to certain events such as device-detected AF events of a particular confidence level. Consequently, medical resources may be better aligned to serve more patients, and the patient management cost in a healthcare facility may be reduced.

FIG. 1 illustrates generally an example of a patient management system 100 and portions of an environment in which the system 100 may operate. The patient management system 100 may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event using the sensed physiologic signal. In an example, the physiologic event includes a cardiac arrhythmic event, such as atrial fibrillation (AF), atrial flutter, atrial tachycardia, supraventricular tachycardia, ventricular tachycardia, or ventricular fibrillation, cardiac pauses, among other brady- or tachy-arrhythmia. In some examples, the physiologic event detector circuit 160 may operate in a patient-triggered mode, register a patient-triggered event, and record physiologic data in response to a user-activated trigger. The trigger may be activated by the patient when the patient demonstrates signs or symptoms, or experiences a precursor event indicative of a medical event.

In some examples, the physiologic event detector circuit 160 may extract from the sensed physiologic signal a signal characteristic, and determine a confidence indicator for the detected physiologic event using the signal characteristic. The confidence indicator indicates a likelihood that the detected physiologic event is present. The confidence indicator may have a categorical or numerical value. In an example, the detected physiologic event is an AF event, and the signal characteristic may be extracted from an atrial activation event, such as a P wave detected from a subcutaneous ECG signal. The physiologic event detector circuit 160 may determine an AF confidence indicator for the detected AF event using the characteristic of the atrial activation event. Alternatively, in some examples, the confidence indicator for the physiologic event detected by AMD 110 may be evaluated by an external device, such as one in the external system 125. Examples of the AF confidence and applications thereof are discussed below with reference to FIGS. 2-4.

The AMD 110 may alternatively be configured as a therapeutic device configured to treat arrhythmia or other heart conditions. The AMD 110 may include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event events, may be collected by the AMD 110, among other data acquisition sensors or devices associated with the patient 102. The remote device 124 may include a storage unit to store the patient data in a patient database. The remote device 124 may include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the AMD 110. By way of example, alert notifications may include a Web page update, phone or pager call, E-mail, SMS, text, or "Instant" message, as well as a message to the patient and a simultaneous direct notification to emergency services and to the clinician. Other alert notifications are possible.

In some examples, the external device 120 or the remote device 124 may include a medical event prioritizer circuit configured to prioritize the alert notifications. Prioritization of the alert notifications may be based on a confidence indicator of the physiologic event being detected. In an example of detecting AF events, an AF confidence indicator may be generated based on a signal characteristic of an atrial activation event, such as a P wave detected from a subcutaneous ECG signal sensed by the AMD 110. The confidence indicator may be generated by the AMD 110, or alternatively by the external device 120 or the remote device 124. In the event that multiple arrhythmic events (e.g., multiple AF events) are detected with respective confidence indicators, the alert notifications and the physiologic signals associated with the arrhythmic events may be prioritized in a specific order (e.g., a descending order, or an ascending order) of confidence indicators. The arrhythmic events may be presented to a user for event review or adjudication, or to a process for arrhythmia confirmation, in accordance with the prioritized order.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
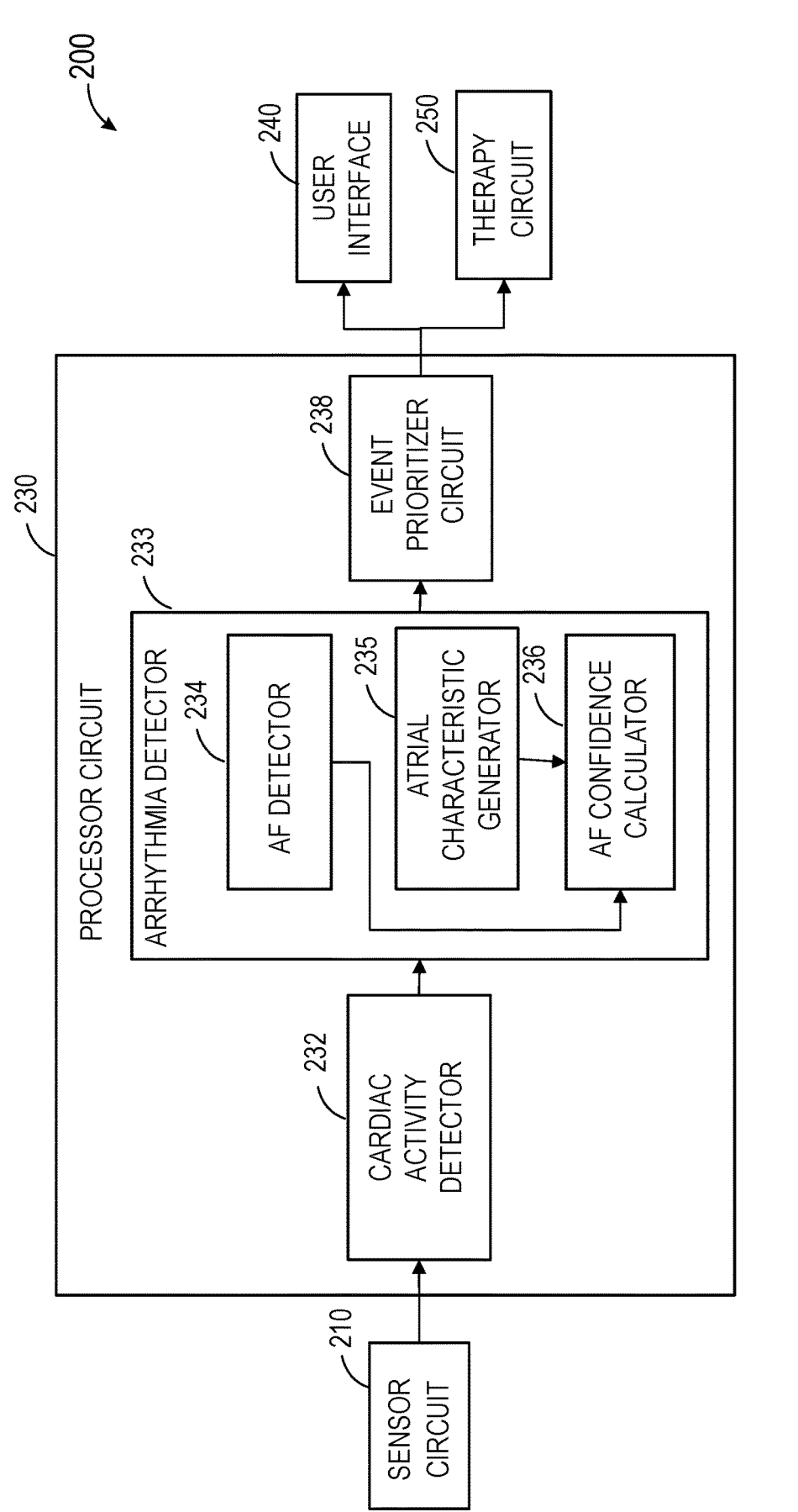
FIG. 2 illustrates generally an example of an arrhythmia detection system configured to detect an arrhythmia event, such as an AF event.

FIG. 2 illustrates generally an example of an arrhythmia detection system 200 configured to detect a cardiac arrhythmia event, such as an AF event. Portions of the system 200 may be included in the physiologic event detector circuit 160 of the AMD 110, or the external system 125. The system 200 may include one or more of a sensor circuit 210, a processor circuit 230, and a user interface unit 240. The system 200 may additionally include an optional therapy circuit 250.

The sensor circuit 210 may include circuitry configured to sense a physiologic signal sensed from a patient via one or more implantable, wearable, or otherwise ambulatory sensors or electrodes associated with the patient. The sensors may be incorporated into, or otherwise associated with an ambulatory device such as the AMD 110. In some examples, the sensors may be incorporated into an implantable cardiac monitor (ICM) device configured for subcutaneous implantation. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more sub-circuits to digitize, filter, or perform other signal conditioning operations on the received physiologic signal.

The processor circuit 230, coupled to the sensor circuit 210, may detect an arrhythmic event, and generate an event priority for the detected arrhythmic event. By way of example and not limitation, the processor circuit 230 may be configured to detect and analyze an AF event. The processor circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 230 may include circuit sets comprising one or more other circuits or sub-circuits, including a cardiac activity detector 232, an arrhythmia detector circuit 233, and an event prioritizer circuit 238. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The cardiac activity detector 232 can detect a cardiac activity, such as an atrial activation event, using one or more physiologic signals sensed by the sensor circuit 210. In an example, the sensor circuit may be coupled to one or more implantable, wearable, or otherwise ambulatory cardiac activity sensors configured to sense cardiac electrical or mechanical activity from the patient. Examples of the cardiac electrical activity may include an ECG sensed using surface electrodes or subcutaneous electrodes, or intracardiac EGM sensed from inside the heart chamber or heart tissue using intracardiac electrodes. Examples of cardiac mechanical activity may include a heart sounds (HS) signal such as sensed using an accelerometer or a microphone to sense cardiac vibrational or acoustic information, a cardiac impedance signal that varies with cyclic cardiac contractions which may be sensed using an impedance sensor, or a pressure signal that varies with arterial pulses which may be sensed using a pressure sensor, among others.

In an example, the cardiac activity detector 232 may detect a ventricular activation event and an atrial activation event from a surface ECG signal, a subcutaneous ECG signal, or an intracardiac EGM signal. The ventricular activation event includes a QRS complex representing a ventricular depolarization, and the atrial activation event includes a P wave preceding the QRS complex in the same cardiac cycle and representing an atrial depolarization. Depending on the sensing vector (e.g., electrodes positions) for sensing the ECG signal, QRS complexes (or the R waves) may have larger peak amplitudes than P waves. In an example, the cardiac activity detector 232 may compare the cardiac electrical signal to a threshold to detect a ventricular activation event (e.g., R wave peak), and define an atrial detection window ($W_A$) preceding the detected ventricular activation event within the same cardiac cycle. In an example, the atrial detection window is approximately 120-200 milliseconds (msec) preceding the detected R wave peak. In another example, the atrial detection window is approximately 50-200 msec preceding the detected R wave peak. The cardiac activity detector 232 may detect an atrial activation event (e.g., a P wave) using the portion of the cardiac electrical signal within the atrial detection window $W_A$. In an example, the atrial activation event may be detected based on a peak intensity, such as a peak amplitude or a peak signal power, of the signal portion within the atrial detection window. In another example, the cardiac activity detector 232 may detect an atrial activation event based on a dominant frequency of the portion of the cardiac electrical signal within the atrial detection window.

In some examples, the cardiac electrical signal may be preprocessed to improve signal quality prior to detecting ventricular and atrial activation events. The preprocessing may include signal filtering to improve a signal-to-noise ratio. In an example, the cardiac activity detector 232 may determine a noise characteristic, such as a noise level, of the sensed cardiac electrical signal within a noise window, and filter the sensed cardiac electrical signal using the detected noise level. In an example, the cardiac activity detector 232 may use an adaptive filter to cancel or attenuate the noise iteratively. The adaptive noise cancellation may involve a primary input containing noise-contaminated ventricular and atrial activation signals, and a reference input containing noise correlated with the noise in the primary input. The reference input may be adaptively filtered and subtracted from the primacy input to obtain a filtered cardiac activity signal free of or less interfered by noise. Ventricular and atrial activation events may then be detected from the filtered signal.

In some examples, the physiologic signals acquired from a patient may be stored in a storage device such as an electronic medical record system. The sensor circuit 210 may retrieve a physiologic signal from the storage device in response to a command signal that is provided by a system user, or automatically generated in response to occurrence of a trigger event.

The arrhythmia detector circuit 233 may be configured to determine a confidence for a device-detected AF event. Information about the device-detected AF event may be received from a device or a storage device, or be detected by the arrhythmia detector circuit 233. In an example where the system 200, or a portion thereof including the processor circuit 230, is implemented in the external system 125, the device-detected AF event can be detected by a device, such as the AMD 100. In an example as illustrated in FIG. 2, the arrhythmia detector circuit 233 may include an AF detector 234 configured to detect an AF event. In an example, the AF event may be detected using ventricular rate stability. Ventricular cycle length in cardiac cycles may be computed from a cardiac signal representative of ventricular electrical or mechanical activation, such as an ECG, a cardiac imped-ance signal, or a heart sound signal, among other signals. The ventricular rate stability may be computed using a relative difference, a range, a variance, or a standard devia-tion of the ventricular cycle length between cardiac cycles, such as consecutive cardiac cycles. In an example, the ventricular rate stability may be computed using a metric derived from a histogram or a statistical distribution of ventricular cycle length over multiple cardiac cycles, among other variability measures or second-order statistics. The AF detector 234 may detect an AF event if the ventricular rate variability exceeds a threshold or is within a value range. In some examples, the AF detector 234 may detect an AF event using morphology of cardiac signals.

In an example, the AF detector 234 may detect an AF event using a ventricular rate pattern of consecutive decrease in ventricular rate. The ventricular rate pattern includes a pair of consecutive ventricular rate changes. Both ventricu-lar rate changes are negative, referred to as a "double decrement" ventricular rate pattern. A double-decrement ratio, which represents a prevalence of the double decrement ventricular rate pattern over a specified time period or over a plurality of ventricular beats, may be computed, and used to detect AF. Krueger et al. U.S. patent application Ser. No. 14/825,669, entitled "ATRIAL FIBRILLATION DETEC-TION USING VENTRICULAR RATE VARIABILITY," refers to double decrement pattern in ventricular heart rate and its use in atrial arrhythmia detection, the disclosure of which is incorporated by reference herein in its entirety.

In an example, the AF detector 234 may detect an AF event using a ventricular rate cluster, represented by a statistical distribution or a histogram of ventricular rate or cycle length over multiple cardiac cycles. The ventricular rate cluster indicates regularity of ventricular rates of cardiac cycle lengths. Patients with AF are typically presented with irregular ventricular contractions. However, premature atrial contractions (PACs) may occur at irregular intervals. When PACs conduct to the ventricle, they may produce irregular ventricular rates, resulting in different ventricular clusters than AF. As such, the ventricular rate clusters may be used to distinguish frequent PACs from an AF event. Per-schbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

In an example, the AF detector 234 may detect an AF event using a metric representing the occurrence of various beat patterns of the cycle lengths or heart rates. For example, the beat pattern may include a number or percentage of consecutive heart beats with each time period (e.g., a 2-min-ute time windows) that are within +/−5 bpm. In an example, the statistical measure includes an atrioventricular (AV) conduction block metric indicating a presence or degree of conduction abnormality during a sinus rhythm, such as a Wenckebach score representing the prevalence of Wencke-bach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety.

As illustrated in FIG. 2, the arrhythmia detector circuit 233 may include an atrial characteristic generator 235 and an AF confidence calculator 236. The atrial characteristic gen-erator 235 can generate a signal characteristic from the detected atrial activation event. Based on the signal charac-teristic of the atrial activation event, the AF confidence calculator 236 can generate a confidence indicator for a device-detected AF event. The AF confidence indicator may have categorical or numerical value. In an example, the AF confidence calculator 236 may calculate a numerical confi-dence score as a function of the signal characteristic of the atrial activation event. The AF confidence calculator 236 may compare the confidence score against one or more threshold values, and categorize the confidence into one of a plurality of confidence categories, such as a high confi-dence, a medium confidence, or a low confidence.

During normal sinus rhythm (NSR), the sinoatrial node fires and activates the atrium and directs the electrical rhythm. Effective depolarization of the entire atrium may be reflected on the cardiac electrical signal as a prominent atrial activation event (e.g., P wave). In contrast, during AF, many different impulses rapidly fire at once, causing very fast, chaotic activations in the atria. Because the electrical impulses are so fast and chaotic, no propagatable action potentials may be generated to effectively depolarize the entire atrium. Consequently, no atrial activation event, or a substantially weaker atrial activation event, may be detected from the cardiac electrical signal electrical signal. The present inventor has recognized that the characteristics of the atrial activation event may be indicative of a presence or absence of AF, and may further be used to determine a confidence level of an AF event.

In an example, the sensed cardiac electrical signal may be partitioned into segments corresponding to a plurality of cardiac cycles. The arrhythmia detector circuit 233 may detect an atrial activation event from an ensemble average of the segments of the cardiac electrical signal. In an example, the atrial characteristic generator 235 may measure a peak intensity of the atrial activation event within the atrial detection window $W_A$ (hereinafter "atrial peak intensity"). An example of the atrial peak intensity is a peak signal amplitude. The AF confidence calculator 236 may calculate an AF confidence score as a function of the atrial peak intensity. In an example, the AF confidence score is inversely proportional to the atrial peak intensity, such that a higher AF confidence score may be assigned to an AF event that has a lower atrial peak intensity in the ensemble-averaged cardiac electrical signal.

In some examples, the atrial characteristic generator 235 may measure a signal power of the atrial activation event within the atrial detection window $W_A$. For an AF event, the portion of the ensemble-averaged cardiac electrical signal within the atrial detection window may have little fluctuation in amplitude, thus a weak signal power. The AF confidence calculator 236 may calculate an AF confidence score as a function of the signal power of the portion of the ensemble-averaged cardiac electrical signal within the atrial detection window $W_A$ (hereinafter "atrial signal power"). In an example, the AF confidence score is inversely proportional to the atrial signal power, such that a higher AF confidence score may be assigned to a device-detected AF event with a lower atrial signal power. Examples of the ensemble-averaged cardiac electrical signal and determination of AF confidence indicator based on characteristics of atrial activation event are discussed below, such as with reference to FIGS. 3A-3D.

In some examples, in addition to the atrial signal energy within the atrial detection window $W_A$, a reference signal energy may be computed using a portion of the ensemble-averaged cardiac electrical signal within a reference window $W_R$. The reference window $W_R$ may be prior to, and within the same cardiac cycle as, an R wave. The reference window $W_R$ may have a window length identical to that of the atrial detection window $W_A$, such as 150 msec in an example. In contrast to the atrial detection window $W_A$ which is a time period during which an atrial activation event is likely to be detected if the underlying rhythm is AF, the reference window $W_R$ may be chosen as a time period during which an atrial activation would not be detected even if an AF event is present. In an example, the reference window $W_R$ is approximately 250-400 msec before the R wave, compared to the atrial detection window $W_A$ of 50-200 msec before the same R wave. The AF confidence calculator 236 may compute the atrial signal power $P_{WA}$ within the atrial detection window $W_A$ and a reference signal power $P_{WR}$ within the reference window $W_R$. If $P_{WA}$ is substantially higher than $P_{WR}$ (e.g., the difference between the two exceeds a specific margin), then an atrial activation event (e.g., a P wave) is likely present; accordingly, the rhythm is less likely an AF event. If $P_{WA}$ is substantially the same as $P_{WR}$ (e.g., the difference between them falls below a threshold), then an atrial activation event is likely absent; accordingly, the rhythm is more likely an AF event. The AF confidence calculator 236 may calculate an AF confidence score based on a comparison between $P_{WA}$ and $P_{WR}$. In an example, the AF confidence score ($C_{AF}$) may be calculated as a function ('$f$') of the difference between $P_{WA}$ and $P_{WR}$. In an example, the AF confidence score is inversely proportional to the difference between $P_{WA}$ and $P_{WR}$.

In addition to or in lieu of signal characteristics of atrial activation events derived from an ensemble-averaged cardiac electrical signal, the arrhythmia detector circuit 233 may determine an AF confidence based on consistency or variability of signal characteristics respectively derived from a plurality of atrial activation events. The arrhythmia detector circuit 233 may detect atrial activation events respectively from segments of the sensed cardiac electrical signal in a plurality of cardiac cycles. The atrial characteristic generator 235 may generate respective signal characteristics from the atrial activation events. As described above, the signal characteristics may include an atrial peak intensity or an atrial signal power within an atrial detection window. The AF confidence calculator 236 may determine an AF confidence indicator based on the variability of the signal characteristics of the plurality of atrial activation events. Examples of the variability may include a standard deviation, variance, range, or interquartile range (IQR), among others.

In some examples, the signal characteristics of the atrial activation events may include signal morphologies of a plurality of atrial activation events. In an example, for an atrial activation event $A_i$, a corresponding atrial signal morphology may be represented by a feature vector $X_i$ of N morphological features or data samples $\{X_i(1), X_i(2), \ldots, X_i(N)\}$ taken from the signal portion within the atrial detection window $W_i$. The atrial characteristic generator 235 may generate, from an ensemble average of the signal portions over a plurality of atrial activation events, an ensemble-averaged morphological feature vector $\overline{X} = \{\overline{X}(1), \overline{X}(2), \ldots, \overline{X}(N)\}$. The atrial characteristic generator 235 may calculate similarity metrics (S) between the ensemble-averaged morphological feature vector $\overline{X}$ and each of the N signal morphological feature vectors: $S(\overline{X}, X_1)$, $S(\overline{X}, X_2)$, $\ldots$, $S(\overline{X}, X_N)$. The AF confidence calculator 236 may determine the AF confidence indicator $C_{AF}$ based on the variability ("var") of the N similarity metrics corresponding to the N atrial activation events, such as a function '$f$' of such variability as shown in Equation (1) below:

$$C_{AF} = f(\text{var}\{S(\overline{X},X_1),S(\overline{X},X_2), \ldots ,S(\overline{X},X_N)\}) \qquad (1)$$

In some examples, the atrial characteristic generator 235 may create a template of atrial morphology during a specific type of cardiac rhythm, such as during a normal sinus rhythm (NSR). The atrial morphology template may be represented by a feature vector $X_{Temp}=\{X_{Temp} (1), X_{Temp} (2), \ldots, X_{Temp} (N)\}$. The atrial characteristic generator 235 may calculate similarity metrics (S) between the atrial morphology template $X_{Temp}$ and each of the N atrial morphological feature vectors: $S(X_{Temp}, X_1)$, $S(X_{Temp}, X_2)$, ..., $S(X_{Temp}, X_N)$. The AF confidence calculator 236 may determine the AF confidence indicator based on the variability of the N similarity metrics, such as a function 'f' of such variability as shown in Equation (2) below:

$$C_{AF}=f(\text{var}\{S(X_{Temp},X_1),S(X_{Temp},X_2), \quad . \quad . \quad . \quad , \\ S(X_{Temp},X_N)\}) \qquad (2)$$

The variability metrics calculated according to Equations (1) and (2) indicate variability in atrial morphologies over time in a patient. Examples of the variability "var" may each include a standard deviation, variance, range, or interquartile range (IQR), among others. In an example, the AF confidence score may be directly proportional to the variability of the similarity metrics, such that a higher AF confidence score may be assigned to a device-detected AF event with a higher variability in morphology.

Such a variability measure indicates a degree of variability of consistency in atrial morphologies. In an example, the AF confidence score may be directly proportional to the variability of the similarity metrics, such that a higher AF confidence score may be assigned to a rhythm with a higher variability in morphology.

The event prioritizer circuit 238 may generate an event priority for the AF event based on the AF confidence indicator. In an example, the event prioritizer circuit 238 may include a comparator circuit that compares the AF confidence indicator to one or more threshold values, or ranges of values, to categorize the detected atrial activation event into one of a plurality of priority categories. In some examples, the plurality of priority categories may include a high priority, a medium priority, and a low priority. Other prioritization schemes are also contemplated. In some examples, the arrhythmia detector circuit 233 may determine respective AF confidence indicators for a plurality of AF events. The event prioritizer circuit 238 may prioritize the AF events in a specific order of the AF confidence indicators, such as a descending order, or an ascending order. The ordered AF events may be presented to a user (e.g., displayed on a display) for event review, or for adjudication of arrhythmia detection or classification. The user may rearrange the ordered AF events, or remove one or more AF events from the list being presented. Additionally or alternatively, in some examples, the event prioritizer circuit 238 may provide the ordered AF events to an external device (e.g., the remote device 124) for further data analysis, such as for arrhythmia confirmation. In some examples, the event prioritizer circuit 238 may be configured to store the AF events in a memory device in a manner based on the corresponding confidence indicators. For example, AF events with higher confidence indicators may be stored prior in time to the AF events with lower confidence indicators. In case of a need to release memory space, AF events with lower confidence indicators may be removed from memory before the AF events with higher confidence indicators. In some examples, more memory space may be allocated for AF events with higher confidence indicators than for those with lower confidence indicators.

The user interface unit 240 may include an input device and an output device. In an example, at least a portion of the user interface unit 240 may be implemented in the external system 125. The input device may receive a user's programming input, such as parameters for detecting atrial activation event, generating characteristics of the atrial activation event, or the parameters for determining AF confidence indicator. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmic events, such as the AF events. The output device may include a display for displaying the sensed physiologic information, intermediate measurements or computations, the detected AF events, or the AF confidence indicators for the AF events, among others. An example of a portion of the information being displayed on the display is discussed below with reference to FIG. 4. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 250 may be configured to deliver a therapy to the patient in response to the detected cardiac arrhythmia. Examples of the therapy may include electrostimulation therapy delivered to the heart, a nerve tissue, other target tissues, a cardioversion therapy, a defibrillation therapy, or drug therapy. In some examples, the therapy circuit 250 may modify an existing therapy, such as adjust a stimulation parameter or drug dosage.

Components of the system 200 may be implemented in different devices, such as an ambulatory medical device (e.g., the AMD 110 or an ICM) and one or more devices of an external system (e.g., external device 120 or remote device 124 of external system 125). In an example, the sensor circuit 210 may be included in the ambulatory medical device, while the cardiac activity detector 232, the arrhythmia detector circuit 233 (or a portion thereof), the event priority circuit 238, and the user interface 240 may be included in an external system. In another example, the ambulatory medical device (e.g., the AMD 110 or an ICM) may sense physiologic data, and detect AF events. The detected AF events, including event information such as onset and termination timings, and the patient physiologic data acquired during the detection, may be stored in the memory of the ambulatory medical device. The detected AF events may be downloaded to the remote device 124, such as a server, which includes the cardiac activity detector 232, the atrial characteristic generator 235, the AF confidence calculator 236, and the event prioritizer circuit 238. The remote device 124 may determine, for a plurality of device-detected AF events, respective AF confidence scores based on the signal characteristics of the detected atrial activation events, and prioritize the device-detected AF events in a specific order of AF confidence scores. In some examples, the remote device 124 may perform further data analysis of a portion of the device-detected AF events in the prioritized order, such as confirming the AF events using a different arrhythmia detection or classification algorithm than that used by the ambulatory medical device.

Figure 3A:
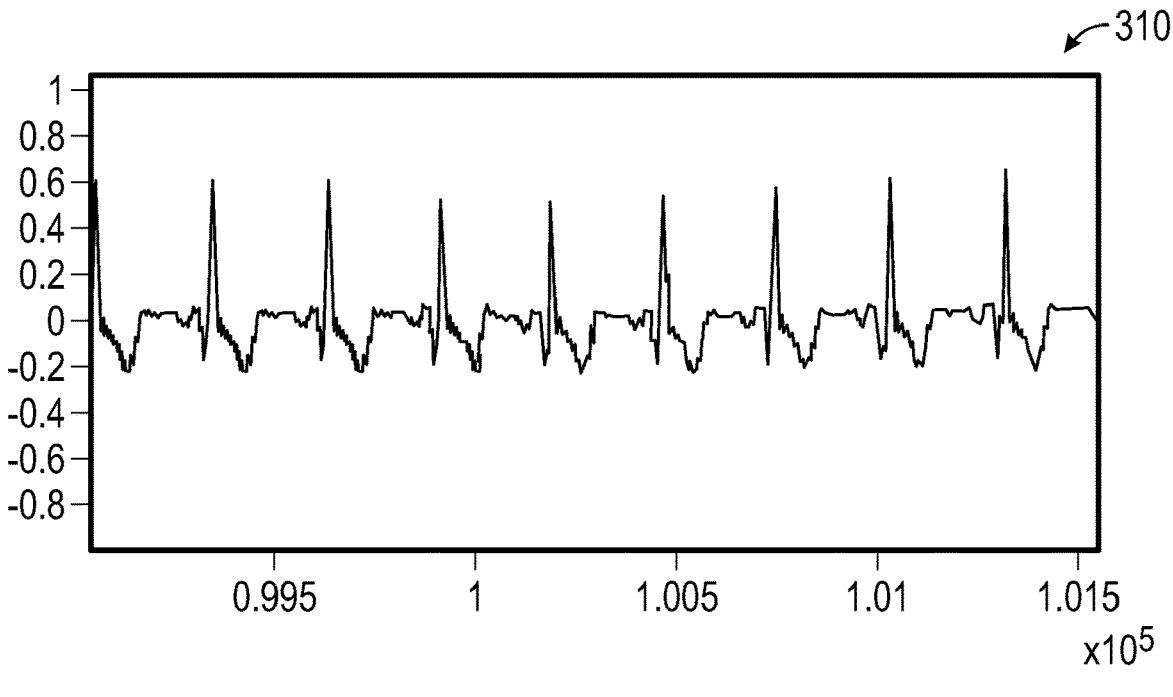
FIGS. 3A-3D are diagrams illustrating examples of cardiac electrical signals sensed from patients and ensemble-averaged cardiac electrical signals.
Figure 3B:
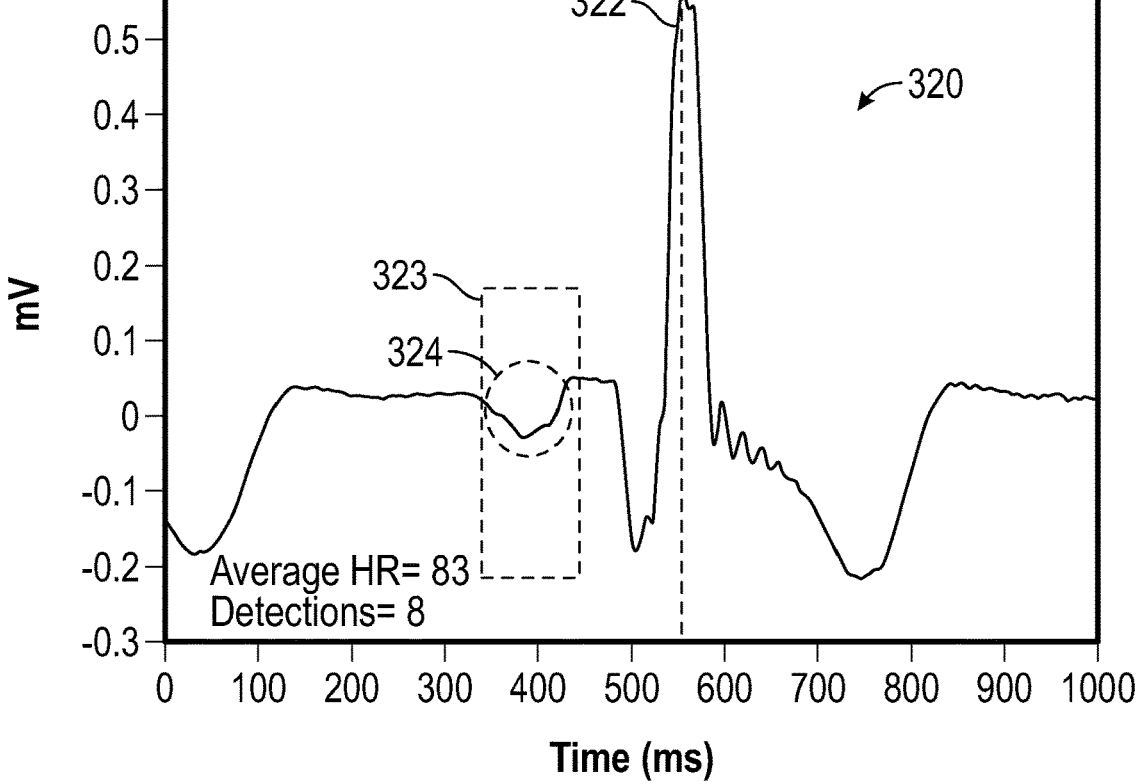
Figure 3C:
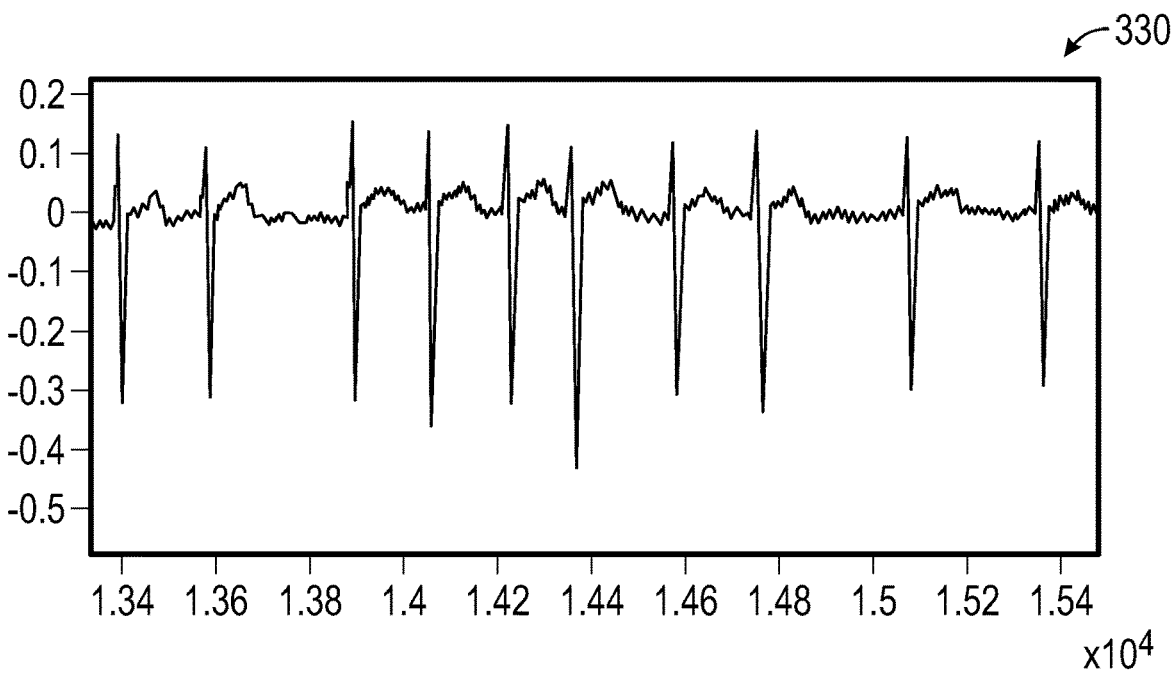
Figure 3D:
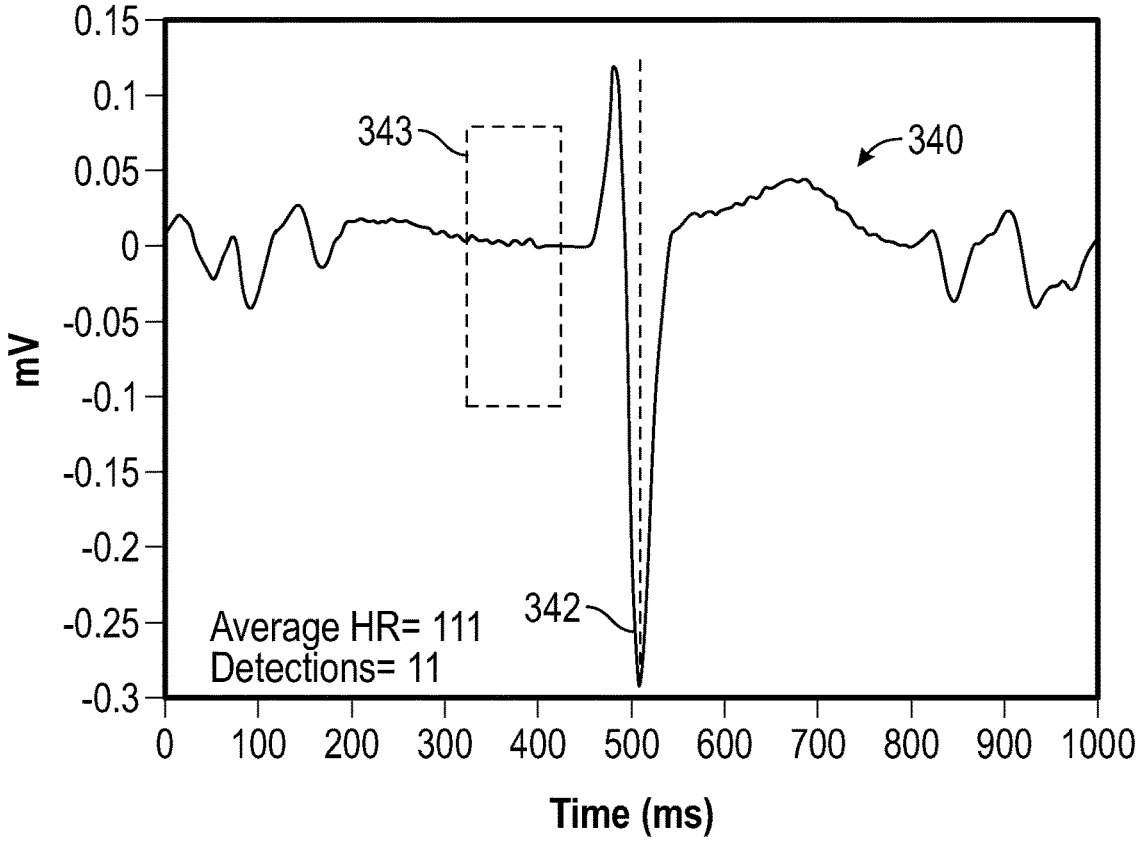

FIGS. 3A-3D are diagrams illustrating examples of cardiac electrical signals acquired from patients that experience different cardiac rhythms, and ensemble averages derived from the respective cardiac electrical signals. The cardiac electrical signals include subcutaneous ECGs sensed by implantable cardiac monitors (ICMs). In particular, FIG. 3A illustrates a portion of a cardiac electrical signal 310 from a patient with a normal sinus rhythm (NSR). FIG. 3B illustrates a waveform 320 of an ensemble average of segments of the cardiac electrical signal 310 corresponding to a plurality of cardiac cycles. FIG. 3C illustrates a portion of a cardiac electrical signal 330 sensed from a patient with chronic AF. FIG. 3D illustrates a waveform 340 of an ensemble average of segments of the cardiac electrical signal 330 corresponding to a plurality of cardiac cycles.

The arrhythmia detector circuit 233 can detect, from the ensemble-averaged waveform 320, a ventricular activation event 322 (e.g., an R wave peak), and define an atrial detection window 323. An atrial activation event 324 may be detected from the ensemble-averaged waveform 320 within the atrial detection window 323. The arrhythmia detector circuit 233 similarly may detect, from the ensemble-averaged waveform 330, a ventricular activation event 342 (e.g., an R wave peak), and define an atrial detection window 343. In contrast to the ensemble-averaged waveform 320 that has a prominent atrial activation event 324 within the atrial detection window 323, no atrial activation event is present on the ensemble-averaged waveform 340 in the atrial detection window 343. The AF confidence calculator 236 may calculate an AF confidence based on the presence/absence of the atrial activation event 324, or a characteristic of the atrial activation event 324 generated by the atrial characteristic generator 235, such as a peak intensity or signal power of the atrial activation event 324, as discussed above with reference to FIG. 2.

Figure 4:
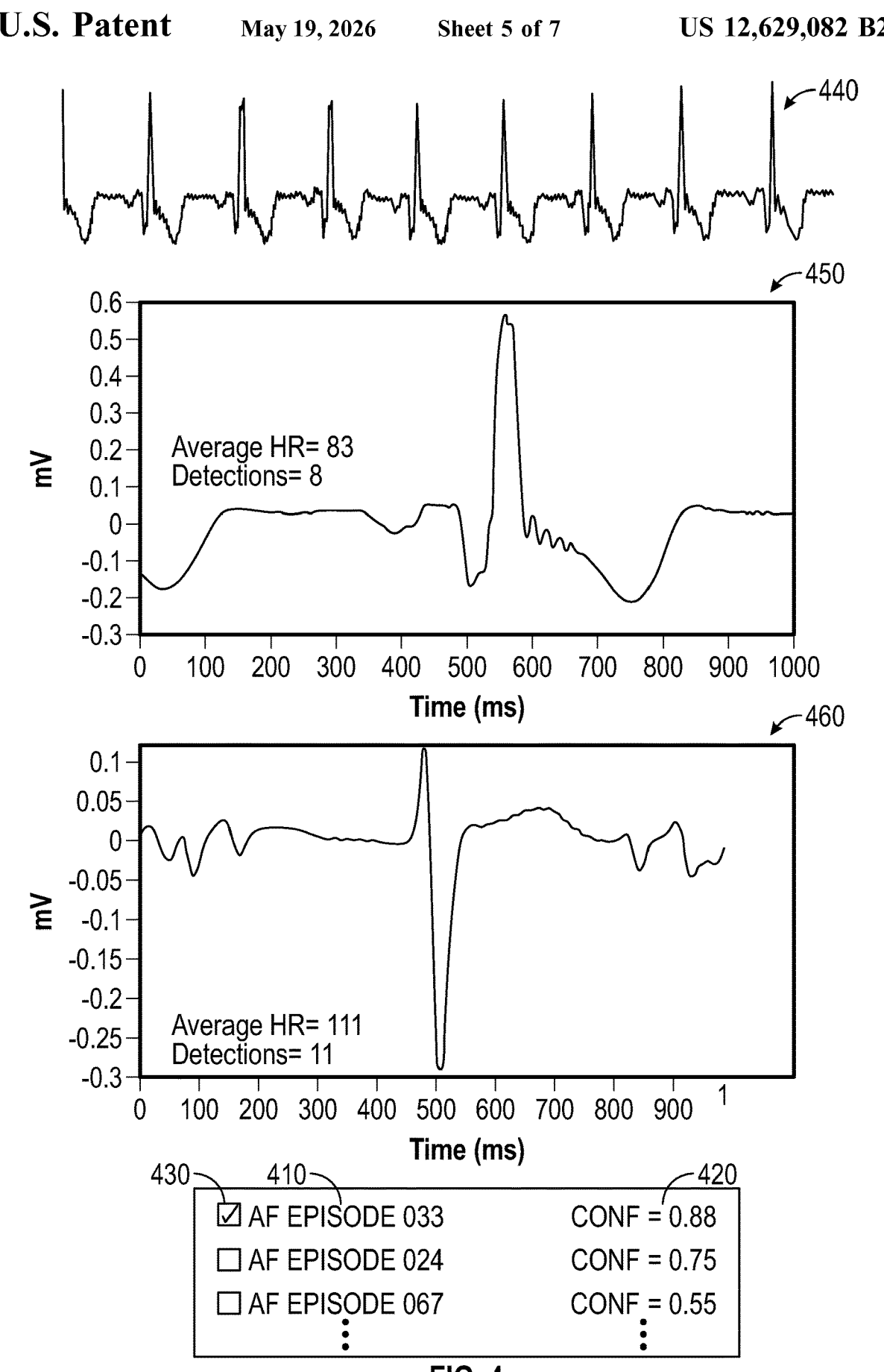
FIG. 4 is an example of prioritized device-detected arrhythmia events being displayed on a display unit of the user interface.

FIG. 4 is an example illustrating prioritized device-detected arrhythmia events being displayed on a display unit of the user interface 240. In this example, information being displayed includes a plurality of AF events identifiers 410 and corresponding AF confidence scores 420, such as determined by the AF confidence calculator 236. The confidence score 420 have numerical values between 0 and 1, representing a probability of the corresponding device-detected event being an AF event. Alternatively, the confidence indicators 420 may have categorical values. The AF event identifiers 410 may be arranged in accordance with the AF confidence indicators, such as in a list of a particular order of the AF confidence indicators. In the example as shown in FIG. 4, the AF event identifiers 410 are arranged in a descending order of the AF confidence indicators. AF events with higher confidence scores are listed on the top of the list before the AF events with lower confidence scores. Alternatively, the AF event identifiers 410 may be arranged in an ascending order of the AF confidence indicators.

A user may use an input device to select an event to view, such as by clicking on a selection box 430 next to the corresponding AF event identifier. In response to the user selection, physiologic data associated with the selected AF event, such as a portion of the cardiac activity signal 440 (e.g., a subcutaneous ECG), may be displayed on the display unit. The displayed signal may include portions showing the arrhythmia onset, continuation, and termination. An ensemble averaged waveform 450 may be generated using segments of the cardiac electrical signal 440 corresponding to a plurality of cardiac cycles, and displayed on the display unit. In some examples, an ensemble averaged waveform 460 derived from non-AF segments, such as data segments prior to the AF onset or post the AF termination, may be displayed on the display unit.

Figure 5:
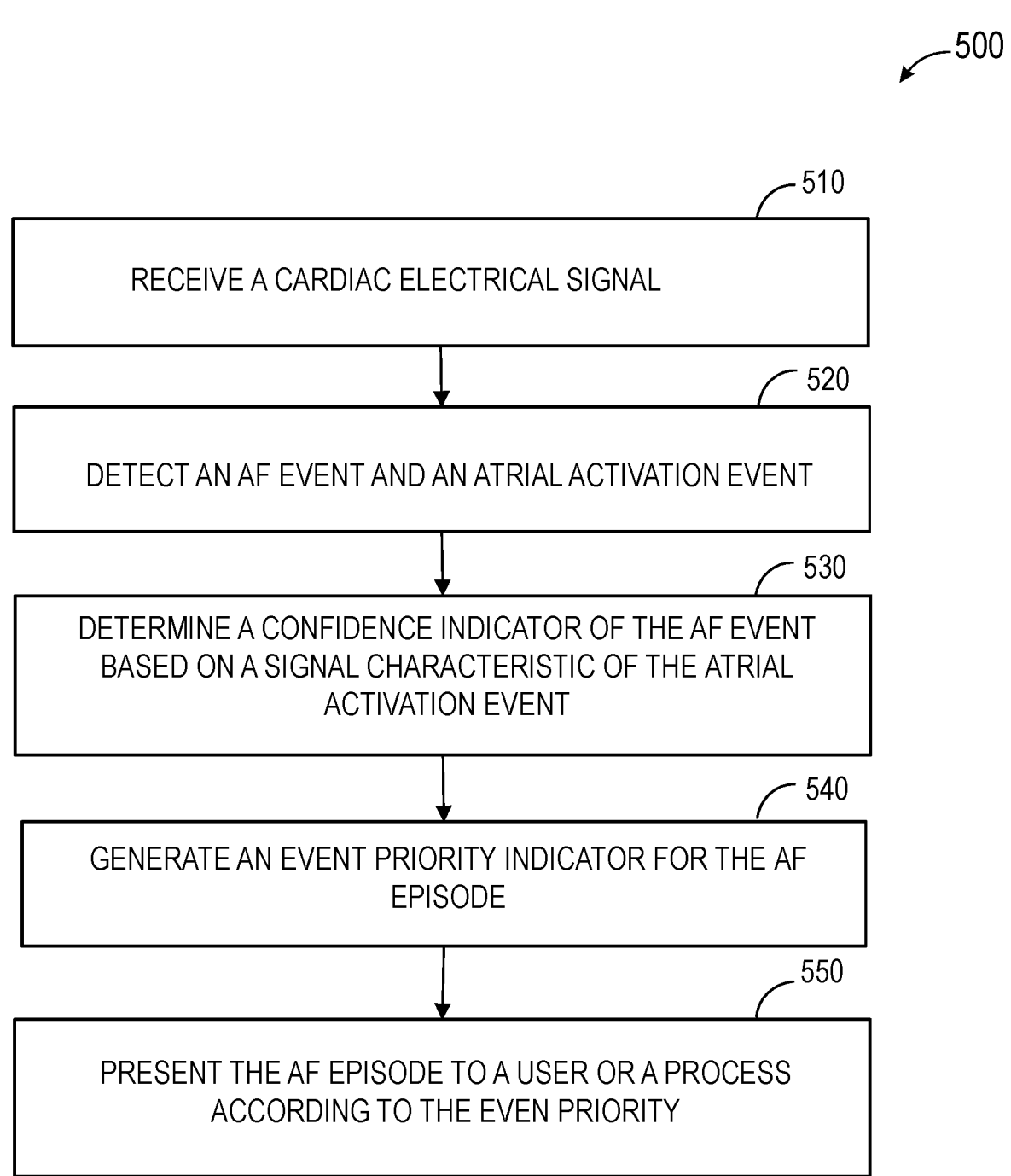
FIG. 5 is a flowchart illustrating an example of a method for detecting a cardiac arrhythmia event, such as an atrial tachyarrhythmia event, in a patient.

FIG. 5 is a flow chart illustrating an example of a method 500 for detecting a cardiac arrhythmia event, such as an AF event. The method 500 may be implemented and executed in an ambulatory medical device such as an implantable or wearable medical device, or in a remote patient management system. In an example, the method 500 may be implemented in and executed by the physiologic event detector circuit 160 of the AMD 110, the external system 125, or the arrhythmia detection system 200.

The method 500 commences at 510, where a physiologic signal sensed from the patient may be received. The physiologic signal may be sensed from a sensor associated with a patient, or be retrieved from a storage device (e.g., an electronic medical record system) that stores physiologic signals recorded from a patient. In an example, the physiologic signal may include a cardiac electrical signal, such as an ECG or an intracardiac EGM. In some examples, the physiologic signal may include thoracic or cardiac impedance signal, arterial pressure signal, pulmonary artery pressure signal, left atrial pressure signal, RV pressure signal, LV coronary pressure signal, heart sounds or endocardial acceleration signal, physiologic response to activity, apnea hypopnea index, one or more respiration signals such as a respiration rate signal or a tidal volume signal, among others. The sensed physiologic signal may be pre-processed, including one or more of signal amplification, digitization, filtering, or other signal conditioning operations.

At 520, an AF event may be detected using a cardiac signal, such as from an ECG, a subcutaneous ECG, an intracardiac EGM, or other cardiac electrical signals received from the patient at 510. The AF event may be detected based on ventricular rate stability, a ventricular rate pattern, a ventricular rate cluster, among other techniques such as described above with reference to the AF detector 234 of FIG. 2. In some examples, the AF event may be detected by a device, and the information about the AF event may be stored in a storage device. An atrial activation event may be detected at 520 using the cardiac signal. In an ECG or subcutaneous ECG, the atrial activation event may be represented by a P wave preceding a QRS complex in the same cardiac cycle. To detect the atrial activation event, in an example, a ventricular activation event, such as a QRS complex, may be detected first such as by using a threshold detector. Then, an atrial detection window preceding the detected ventricular activation event may be defined. The atrial detection window is approximately 120-200 milliseconds (msec) preceding the detected R wave in one example, or 50-200 msec preceding the detected R wave in another example. The atrial activation event may be detected based on a peak intensity, a signal power, or a dominant frequency of the sensed cardiac electrical signal within the atrial detection window.

At 530, an AF confidence indicator may be determined based at least on a signal characteristic of the detected atrial activation event, such as by using the AF confidence calculator 236. In an example, the sensed cardiac electrical signal may be partitioned into segments corresponding to a plurality of cardiac cycles. An atrial activation event may be detected from an ensemble average of the segments of the cardiac electrical signal, such as described above with reference to FIGS. 3A-3D. The AF confidence indicator indicates a likelihood of an AF event being present, and may have a numerical value, also referred to as a confidence score. Alternatively, the AF confidence indicator may have categorical values, such as high, medium, or low confidence categories. An AF confidence score may be computed using a function of the signal characteristics of the atrial activation event (e.g., P wave) detected from the ensemble-averaged cardiac electrical signal. In an example, an AF confidence score is inversely proportional to the atrial peak intensity within the atrial detection window. In another example, an AF confidence score is inversely proportional to the signal power of the portion of the ensemble-averaged cardiac electrical signal within the atrial detection window.

The AF confidence may additionally or alternatively be determined based on consistency or variability of signal characteristics across a plurality of atrial activation events such as detected respectively from segments of the sensed cardiac electrical signal corresponding to a plurality of cardiac cycles. An AF confidence score may then be determined based on a variability of the signal characteristics of the plurality of atrial activation events. In an example, the signal characteristics of the atrial activation events may include signal morphologies of a plurality of atrial activation events. Similarity metrics between the ensemble-averaged morphology and the individual signal morphologies for the plurality of atrial activation events may be computed, and an AF confidence score may be computed using a variability of the similarity metrics corresponding to the plurality of atrial activation events. In some examples, an atrial morphology template acquired during a specific type of cardiac rhythm, such as during an NSR, may be created, such as by the atrial characteristic generator 235. Similarity metrics between the atrial morphology template and the individual signal morphologies for the plurality of atrial activation events may be computed, and an AF confidence score may be computed using a variability of the similarity metrics corresponding to the plurality of atrial activation events.

At 540, an event priority may be generated for the AF event based on the AF confidence indicator, such as using the event prioritizer circuit 238. determine, for two or more AF events, respective AF confidence indicators. The two or more AF events may be prioritized in a specific order of the AF confidence indicators. In an example, the AF events may be arranged in a descending order of AF confidence scores. In another example, the AF events may be arranged in an ascending order of the AF confidence scores.

At 550, the AF event may be presented to a user or to a process in accordance with the associated event priority. In an example, the AF event may be arranged in a descending order of the AF confidence indicators, such that AF events with higher confidence scores are listed on the top of the list before those with lower confidence scores. Alternatively, the AF events may be arranged in an ascending order of the AF confidence indicators. The ordered AF events may be presented to a user (e.g., being displayed on a display unit as shown in FIG. 4) for event review or adjudication of arrhythmia detection or classification. In some examples, the ordered AF events may be provided to an external device (e.g., the remote device 124) for further data analysis, such as for arrhythmia confirmation.

The method 500 may include the optional step of delivering a therapy to the patient in response to the detection of the cardiac arrhythmia, such as via the optional therapy circuit 250 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 6:
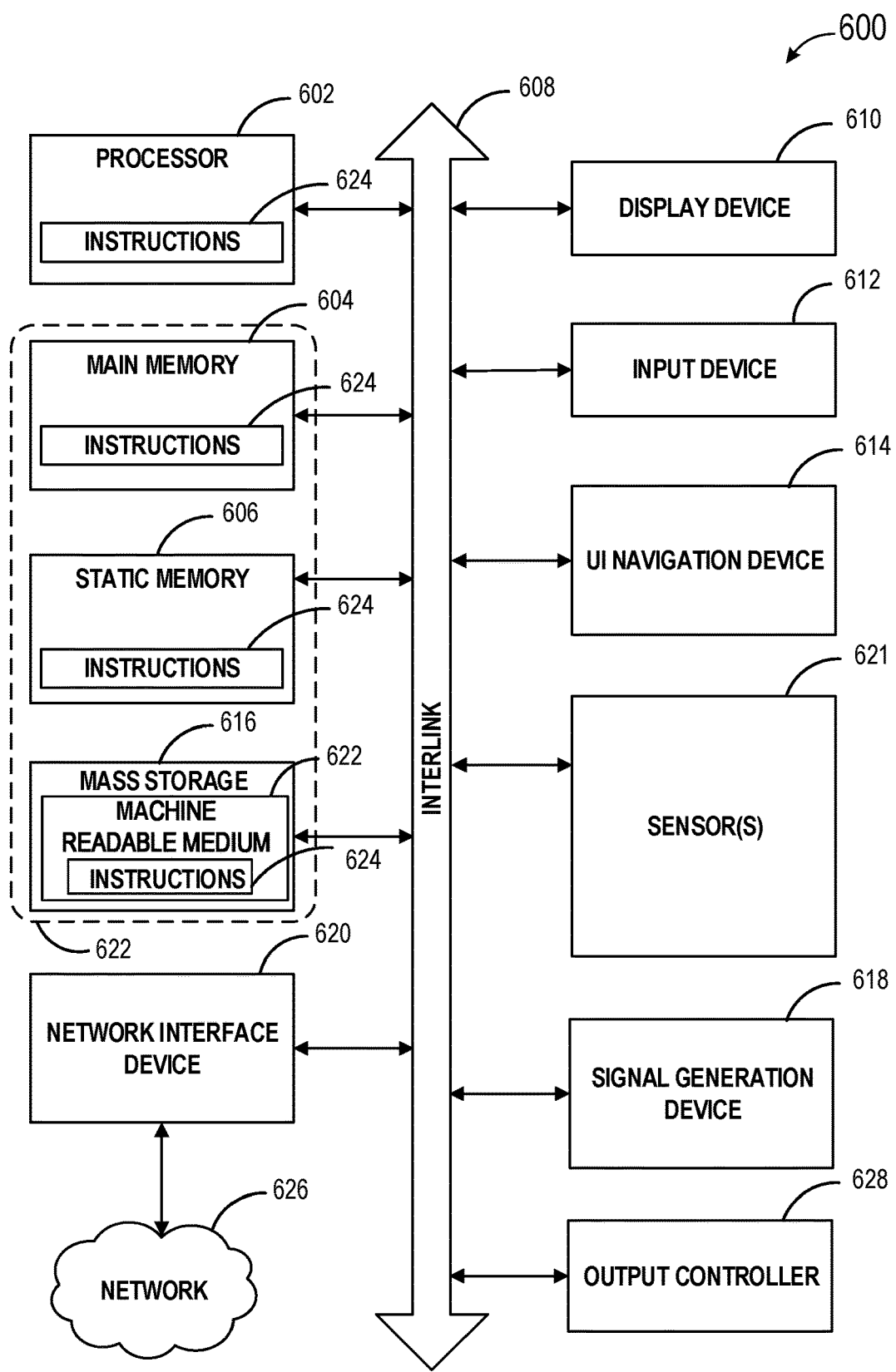
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the AMD 110, or the external system 125.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for detecting cardiac arrhythmia in a patient, the system comprising:
   an atrial fibrillation (AF) detector circuit configured to determine a ventricular rate parameter for the patient using the received cardiac signal and to detect an AF event using the determined ventricular rate parameter;
   an atrial characteristic generator circuit configured to determine an ensemble average of multiple segments of the cardiac electrical signal corresponding to a plurality of cardiac cycles, and to generate a signal characteristic of a P wave for the plurality of cardiac cycles using the determined ensemble average;
   an AF confidence calculator configured to determine an AF confidence indicator indicating a confidence level of the detected AF event based on the ventricular rate parameter of the detected AF event and the signal characteristic of the P wave for the plurality of cardiac cycles comprising the detected AF event;
   an event prioritizer circuit configured to receive the detected AF event in a time-based order corresponding to a time of the detected AF event and to generate an event priority for the detected AF event based on the AF confidence indicator, the event priority different than the time-based order; and
   a controller circuit configured to dynamically control allocation of resources of the medical-device system to process or store information about the AF event, in accordance with the generated event priority, including increasing allocation of resources in response to the generated event priority indicating a high confidence or a numerical confidence score above a threshold in contrast to the generated event priority indicating a low confidence or the numerical confidence score below the threshold, wherein to detect the AF event comprises using information of the cardiac electrical signal separate from the detected absence or presence of the P wave.

2. The system of claim 1, wherein the atrial characteristic generator circuit is further configured to generate the signal characteristic including a peak intensity or a signal power of the detected P wave.

3. The system of claim 1, wherein the atrial characteristic generator circuit is further configured to detect a plurality of P waves respectively from segments of the cardiac electrical signal corresponding to a plurality of cardiac cycles; and generate signal characteristics respectively from the plurality of P waves; and wherein the AF confidence calculator is configured to determine the AF confidence indicator based on a variability of the signal characteristics of the plurality of P waves.

4. The system of claim 3, wherein the atrial characteristic generator circuit is further configured to generate the signal characteristics including similarity metrics between (1) an ensemble-averaged morphology of the plurality of P waves and (2) respective signal morphologies of the plurality of P waves; and wherein the AF confidence calculator is configured to determine the AF confidence indicator based on a variability of the similarity metrics.

5. The system of claim 3, wherein the atrial characteristic generator circuit is further configured to generate the signal characteristics including similarity metrics between (1) an atrial morphology template acquired during a specific type of cardiac rhythm and (2) respective signal morphologies of the P waves; and wherein the AF confidence calculator is configured to determine the AF confidence indicator based on a variability of the similarity metrics.

6. The system of claim 1, wherein the atrial fibrillation (AF) detector circuit is further configured to detect two consecutive ventricular activation events from the cardiac electrical signal;

wherein the atrial characteristic generator circuit is configured to detect the presence or absence of P wave between the detected two consecutive ventricular activation events; and wherein the AF confidence calculator is configured to determine, for the AF event detected using information of the cardiac electrical signal separate from the detected absence or presence of the P wave, the AF confidence indicator including a first AF confidence level in the detected presence of one or more P waves between the detected two consecutive ventricular activation events, and a second AF confidence level in the detected absence of the P wave, the first AF confidence level being lower than the second AF confidence level.

7. The system of claim 6, wherein the atrial fibrillation (AF) detector circuit is further configured to detect an atrial flutter event when more than one P wave is detected to be present between the detected two consecutive ventricular activation events.

8. The system of claim 1, wherein:

the AF confidence calculator is further configured to determine respective AF confidence indicators for two or more AF events detected from the patient; and the event prioritizer circuit is further configured to prioritize the two or more AF events in a descending order of the AF confidence indicators.

9. The system of claim 1, wherein the arrhythmia detector circuit is configured to determine, for the AF event detected using the information of the cardiac electrical signal separate from the detected absence or presence of the P wave, the AF confidence indicator including a first AF confidence level in the detected presence of the P wave and a second AF confidence level in the detected absence of the P wave, the first AF confidence level being lower than the second AF confidence level.

10. The system of claim 9, wherein, in response to the determined AF confidence indicator for the AF event being the first AF confidence level, the arrhythmia detector circuit is configured to confirm the AF event using additional processing that is more computationally intensive than to detect the AF event.

11. The system of claim 1, wherein the medical-device system includes an implantable medical device including the AF detector circuit, the atrial characteristic generator circuit, the AF confidence calculator, the event prioritizer circuit, the controller circuit, and memory.

12. The system of claim 11, wherein the controller circuit is configured to implement dynamic memory management by removing AF events with lower confidence indicators from the memory before removing AF events with higher confidence indicators when memory space needs to be released.

13. The system of claim 1, wherein the controller circuit is configured to dynamically allocate memory space to store the detected AF event based on the generated event priority, including in response to the generated event priority indicating the high confidence or the numerical confidence score above the threshold in contrast to the generated event priority indicating the low confidence or the numerical confidence score below the threshold.

14. A system for detecting cardiac arrhythmia in a patient, comprising:

an ambulatory medical device including a communication circuit and circuitry configured to sense a cardiac electrical signal from the patient, to detect a ventricular rate parameter for the patient using the sensed cardiac electrical signal, and to detect an atrial fibrillation (AF) event using the detected ventricular rate parameter; and an external system communicatively coupled to the ambulatory medical device, the external system including:

an arrhythmia detector circuit configured to:

determine an ensemble average of multiple segments of the sensed cardiac electrical signal corresponding to a plurality of cardiac cycles and to generate a signal characteristic of a P wave for the plurality of cardiac cycles using the determined ensemble average; and determine an AF confidence indicator indicating a confidence level of the detected AF event based on the ventricular rate parameter of the detected AF event and the signal characteristic of the P wave for the plurality of cardiac cycles comprising the detected AF event;

an event prioritizer circuit configured to generate an event priority for the detected AF event based on the AF confidence indicator; and a controller circuit configured to dynamically control allocation of resources of the ambulatory medical device to process or store information about the detected AF event, in accordance with the generated event priority, including increasing allocation of ambulatory medical device resources in response to the generated event priority indicating a high confidence or a numerical confidence score above a threshold in contrast to the generated event priority indicating a low confidence or the numerical confidence score below the threshold, wherein to detect the AF event comprises using information of the cardiac electrical signal separate from the detected absence or presence of the P wave.

15. The system of claim 14, wherein the ambulatory medical device is an implantable cardiac monitor.

16. The system of claim 14, wherein: the arrhythmia detector circuit is further configured to determine respective AF confidence indicators for two or more AF events from the patient;

the event prioritizer circuit is further configured to generate event priorities for the two or more AF events based on the respective AF confidence indicators; and the controller circuit is configured to dynamically control allocation of ambulatory medical device resources for the two or more AF events based on the generated event priorities.

17. A method for detecting cardiac arrhythmia in a patient using a medical-device system, comprising:

receiving a cardiac electrical signal sensed from the patient;

determining a ventricular rate parameter for the patient using the received cardiac electrical signal;

detecting, using an arrhythmia detector circuit, an atrial fibrillation (AF) event using the determined ventricular rate parameter;

detecting, using the arrhythmia detector circuit, a signal characteristic of a P wave from an ensemble average of multiple segments of the received cardiac electrical signal corresponding to a plurality of cardiac cycles;

determining an AF confidence indicator indicating a confidence level of the detected AF event based on the ventricular rate parameter of the detected AF event and the signal characteristic of the P wave for the plurality of cardiac cycles comprising the detected AF event;

receiving the detected AF event in a time-based order corresponding to a time of the detected AF event;

generating, using an event prioritizer circuit, an event priority for the detected AF event based on the AF confidence indicator, the event priority different than the time-based order; and via a controller circuit, dynamically allocating resources of the medical-device system to process or store information about the AF event, in accordance with the generated event priority, including increasing allocation of resources in response to the generated event priority indicating a high confidence or a numerical confidence score above a threshold in contrast to the generated event priority indicating a low confidence or the numerical confidence score below the threshold, wherein detecting the AF event comprises using information of the cardiac electrical signal separate from the detected absence or presence of the P wave.

18. The method of claim 17, wherein the signal characteristic includes a peak intensity or a signal power of the P wave, and the atrial fibrillation (AF) confidence indicator is determined to be inversely proportional to the peak intensity or the signal power of the P wave.

19. The method of claim 17, comprising: sensing, using a sensor of an implantable medical device, the cardiac electrical signal from the patient, wherein the implantable medical device comprises the arrhythmia detector circuit, the event prioritizer circuit, and the controller circuit, wherein dynamically allocating resources of the medical-device system comprises dynamically allocating resources to the implantable medical device, including memory of the implantable medical device to store information about the detected AF event.

* * * * *